United States Patent
Shoenfeld et al.

(10) Patent No.: US 9,195,804 B2
(45) Date of Patent: Nov. 24, 2015

(54) DAISY CHAIN ARRAY OF MEDICATIONS CABINETS

(71) Applicants: Norman A. Shoenfeld, Cypress, TX (US); Christopher Childs, Pen Argyl, PA (US)

(72) Inventors: Norman A. Shoenfeld, Cypress, TX (US); Christopher Childs, Pen Argyl, PA (US)

(73) Assignee: S & S X-Ray Products, Pen Argyl, PA (US)

( * ) Notice: Subject to any disclaimer, the term of this patent is extended or adjusted under 35 U.S.C. 154(b) by 430 days.

(21) Appl. No.: 13/706,733

(22) Filed: Dec. 6, 2012

(65) Prior Publication Data

US 2014/0163726 A1  Jun. 12, 2014

(51) Int. Cl.
*G08B 21/00* (2006.01)
*G06F 19/00* (2011.01)
*G07F 17/00* (2006.01)

(52) U.S. Cl.
CPC ........ *G06F 19/3462* (2013.01); *G07F 17/0092* (2013.01)

(58) Field of Classification Search
None
See application file for complete search history.

(56) References Cited

U.S. PATENT DOCUMENTS

| 5,713,485 | A | 2/1998 | Liff et al. | |
| 6,549,127 | B1 * | 4/2003 | Strackbein et al. | 340/506 |
| 7,587,539 | B2 * | 9/2009 | Picard et al. | 710/104 |
| 8,103,379 | B2 | 1/2012 | Biba et al. | |
| 2006/0192001 | A1 * | 8/2006 | Shaffer et al. | 235/385 |
| 2011/0196538 | A1 * | 8/2011 | Michael | 700/275 |
| 2011/0266929 | A1 * | 11/2011 | Michael | 312/107 |
| 2012/0239840 | A1 * | 9/2012 | Pimputkar et al. | 710/107 |

* cited by examiner

*Primary Examiner* — Mark Rushing
(74) *Attorney, Agent, or Firm* — Bernard P. Molldrem, Jr.

(57) ABSTRACT

A group of locking medical storage are connected together using a daisy-chain connection based on i2C protocol. Each of the storage cabinets has one or more locking compartments. A control PC computer is connected to a first one of the cabinets, and that cabinet is connected to each of the other cabinets using i2C daisy chain cabling. The cabinets each have a control circuit module that controls locking and unlocking of doors and drawers, and sensors to detect open or closed status and locked or unlocked status. RFID readers detect which items or medications have been removed from the cabinet. Each cabinet is assigned a unique independent address for identification when it is joined to the daisy chain, which can include an unlimited number of cabinets.

13 Claims, 5 Drawing Sheets

DAISY CHAIN ARRAY OF MEDICATIONS CABINETS

BACKGROUND OF THE INVENTION

This invention relates to cabinets for storing and dispensing prescription medications, non-prescription pharmaceuticals, catheters, bandages and dressings, medical supplies and other similar items for patient care in a hospital, clinic, nursing home, or similar health care facility. The invention is more specifically directed to an array of medical dispensing cabinets in which cabinet access is controlled, and inventory is maintained at a central hospital location, using software, with bar code scanning or RFID scanning to track authorized persons accessing the cabinet(s) and to track inventory items.

The term medications cabinet, as it appears in this specification, and claims is meant to include any cabinet that may be used for storing health-care related items, not limited to medications, but also including dressings, catheters, gloves, gowns, sterilized medical or dental implements, syringes, or many other items.

More specifically, the invention is directed to a controlled hospital supply storage system in which numerous controlled cabinets are linked together electronically and can be controlled and queried from a given location, and in which additional cabinets may easily be added to (or removed from) the system.

In any hospital or clinic, or in wards or floors of the hospital or health center, controlled access cabinets are used for storage of pharmaceuticals and of other limited-access medical supplies. The medications prescribed for patients need to be conveniently accessible for the authorized nurse staff, but also need to be protected from unauthorized access of prescription medications, controlled substances, and high-value medical supplies. Controlled medical cabinets for storing and dispensing pharmaceuticals and hospital supplies are distributed throughout the hospital, clinic, or other health care facility, so as to be located at or near the point of care, i.e., near the patient to which the pharmaceutical or other medical item is to be administered. These cabinets are desirably networked to a central hospital data system that can control access remotely and can maintain inventory for each cabinet. However, in a typical hospital supply system, the cabinets must each be independently connected with the hospital computer system. If a common type of computer bus is used, e.g., a USB hub, only a limited small number of cabinets can be linked with a given control computer. Current locking cabinets typically incorporate USB connections (for access to a computer) and may incorporate control circuitry with software for controlling unlocking functions and inventory functions. These may be capable of IP addressable configurations. Maintaining an accurate inventory for all the cabinets in the system is critical, so that the cabinets can be filled or replenished by pharmacy staff, and accessed by nursing staff to administer items to patients. The inventory should provide a record of which supplies and which medications are stored, and in what quantities, in which locking (or non-locking) compartments of which cabinet. There is a need for a system of medical supply cabinets that can be easily linked together, using reliable and low-cost communications equipment and cabling, to permit an unlimited number of cabinets to be controlled from a single computer station, using a straightforward software arrangement.

OBJECTS AND SUMMARY OF THE INVENTION

Accordingly, it is an object of the present invention to provide an arrangement of controlled-access cabinets, distributed throughout a hospital or clinical environment, and which can be controlled from a computer device that is connected to one of the cabinets, and which can also obtain inventory and status information for each of the cabinets, and which avoids the drawbacks of the prior art.

It is another object to provide an arrangement of medication storage cabinets and medical supply cabinets which can comprise a large number of cabinets, e.g., fifty or more, all included in an array, using a single PC or similar computer device.

A further object is to provide an array of medical supply cabinets and medication storage cabinets which can be enlarged by simply plugging an additional storage cabinet into any of the other cabinets in the array, with the associated computer unit automatically recognizing the additional cabinet and including it in the array.

In accordance with an aspect of the present invention, a medication dispensing system involves a medical storage cabinet that is connected with one or more additional locking storage cabinets using a daisy-chain connection based on i2C protocol. Each of the storage cabinets has one or more locking doors and/or drawers, and each cabinet is individually powered either by AC mains power, battery power, or power obtained from the daisy chain wiring.

In the i2C communications system, the wiring includes at least a common bus, a serial data bus, and a serial clock bus. There may be a second power bus supplying, e.g., drain voltage $V_{dd}$ or ground.

The cabinets each include a circuit board that controls locking and unlocking of the doors and drawers, sensors to detect if the doors or drawers are open or closed, and sensors to detect if the doors are locked or unlocked. The cabinet may have a bar code reader, RFID reader, or similar device. In most instances a wireless barcode scanner or RFID reader may be used and carried by the pharmacy technician or supply technician to identify the items removed from any of the cabinets in the array. This will communicate back to the single PC attached to the array of cabinets, to record which items or medications have been removed from the cabinet(s).

The PC or other computer device is connected, e.g., with a USB cable, to a first one of the cabinets, and that cabinet is connected to each of the other cabinets using the i2C daisy chain cabling. The terms cable and cabling can include a single group of conductors, or any number of them, as needed to connect the cabinet units together in a daisy-chain arrangement.

In the i2C cable, the serial data and serial clock lines are open drain lines, with pull-up resistors connecting them to the drain voltage $V_{dd}$. The control board in each cabinet has a communications circuit with i2C protocol so that each cabinet's control board can independently gain control of the i2C bus to send and/or receive commands. Each cabinet is assigned a unique independent address for identification to receive specific commands, but can also be responsive to a general call address. The unique independent address is for commands and queries specific to the given cabinet, and the general address is for a general call to communicate with all the cabinets at one time.

After the first cabinet is connected to the computer, the second cabinet (and all other cabinets) will not need any set-up procedure to be able to send and/or receive commands. Then the additional cabinet is immediately ready to receive commands for locking or unlocking the cabinet, or to respond to requests for cabinet status or inventory. When connected by daisy chain to either the first cabinet or any other cabinet in the array, the computer assigns each cabinet its unique independent address and also assigns it the general address. The added cabinet needs no setup to receive commands for locking or unlocking or to be queried or polled as to cabinet status or controls. As an option, the added cabinet can be set up so as to have full status functions of name, location, and inventory control. The additional cabinets can be added to the array with a cable connecting it to any other cabinet in the daisy chain. As the i2C connects the cabinets with the bus, a failure or malfunction of any cabinet will not impair communications to and from the cabinets beyond the malfunctioning cabinet. This would not be the case in a mesh or store-and-forward array. Alternatively, an additional cabinet can be added anywhere by breaking the chain, connecting the new cabinet to the disconnected cable, and adding a cable to the next cabinet. If a ring wiring topology is used, rather than a linear chain, a break in the daisy chain will not disrupt communications.

In an array of this design, when an authorized person, e.g., a nurse or pharmacist, needs to obtain a medication or medical supply item for a given patient, the authorized person accesses the system PC, either by a PC or a touch screen computer tied to the hospital system, or by a barcode scanner or RFID reader on or in the cabinet itself. Then, the PC in the array sends out information along the daisy chain that passes to each of the cabinets.

The PC sends out the following to the cabinets in the array:
1. ID and location for the cabinet.
2. Serial number assigned to the cabinet.
3. Which door or drawer of the addressed cabinet to lock and unlock. The cabinet then provides a lock or unlock command to an associated servomotor or solenoid
4. Which drawer to open.
5. Which bin in a given drawer to open.
6. Which light or LED to turn on to illuminate a given section of the cabinet.

When queried or polled, the cabinets respond by sending back the following information along the i2C daisy chain:
1. Which door is open.
2. Which drawer is open.
3. Status of each lock, i.e., what is the status of the servomotor: whether it is in position to lock or unlock the associated door(s) or drawer(s). This is necessary status information, as a given door may be closed, but with the lock unlocked, or the door can also be open but with the lock in the locked state.
4. The ID or location of the cabinet.
5. The serial number of the cabinet.
6. Revision information, i.e., information as to which firmware or software is resident on the cabinet's control module electronics, and
7. Inventory status, i.e., what item(s) have been removed from the cabinet having RFID capability, and when.

The i2C protocol allows any of the cabinets to be taken off line without disrupting communications between any of the other cabinets. All cabinets are identical and any cabinet may have the PC connected to it, and can serve as "master" with the remaining cabinets being "slave" to it.

In addition to receiving lock and unlock commands, the cabinets and the PC are in communication to identify when a cabinet is on line and powered up, and attached to the daisy chain, and as to the specific ID that is assigned to the cabinet.

Each cabinet has a methodology of securing medications, either with doors, drawers or bins. The doors, drawers and/or bins can all be secured with solenoid locks in combination with rotary latches or motor and hook assemblies. Each cabinet may also contain a refrigerator compartment with a locking mechanism. The refrigerator locking mechanism can be controlled with a USB communications system or a part of the daisy chain communication. All cabinets may have lighting and possibly buzzers to create an alarm signal in the event that a door or drawer is left open. All locks can have a key lock cylinder mechanism for allowing emergency manual override access to the medications, in the case of power failure or PC failure. The daisy chain cable may be any industry standard, e.g., firewire, xlr, etc., containing at least three conductors for common, serial data and serial clock. Preferably, the cabling employed for daisy-chaining is different from the USB cable that is used to connect the first cabinet to the PC, so as to prevent confusion at the user location. For example, where a fire-wire cabling system is used for the daisy chain, the connector is different from the USB connector, and the daisy-chaining cabling cannot be accidentally plugged into the USB port.

In a preferred embodiment, a single PC may be connected with one cabinet and then via the daisy chain with a number of other cabinets. The PC may be part of a wired or wireless network, and may possibly be connected with the hospital pharmacy or clinic pharmacy. Each cabinet is connected to all the others in a daisy chain configuration, by connecting each cabinet with the next. The method of daisy chaining may be linear or ring topology, i.e., with the last cabinet in the series being connected with the first. The one PC or multiple PCs can be connected into this array, without any distinction as to which cabinet is the controlling cabinet. However, in the preferred arrangement, the PC connects to the first cabinet in the daisy chain, and that first cabinet relays all commands to the additional cabinets, using the appropriate addresses. There are two methods of signaling: general call and individual identification. A general call goes to all the connected cabinets, and does not require a set up or identification of any cabinet in the daisy chain. An individual identification signal has the intended cabinet's coded identification in the message header, and is accepted only by that one cabinet in the daisy chain. All locking, lighting, and status can be individually controlled and monitored from the PC that is connected to the first cabinet.

The daisy chain may include fifty cabinets or more, all controlled from one location. With the use of one or more i2C hubs, even more cabinets may be added in. The technique of this invention also avoids the limitations of using multiple USB hubs. In a Windows operation system, there is a limitation to the number of USB hubs that can be used, which confines the number of cabinets to a relatively small total. This system, however, overcomes that limitation.

The above and many other objects, features, and advantages of this invention will become apparent from the ensuing description of a selected preferred embodiment, which is to be considered in connection with the accompanying Drawing.

DETAILED DESCRIPTION OF THE PREFERRED EMBODIMENT

Figure 1:
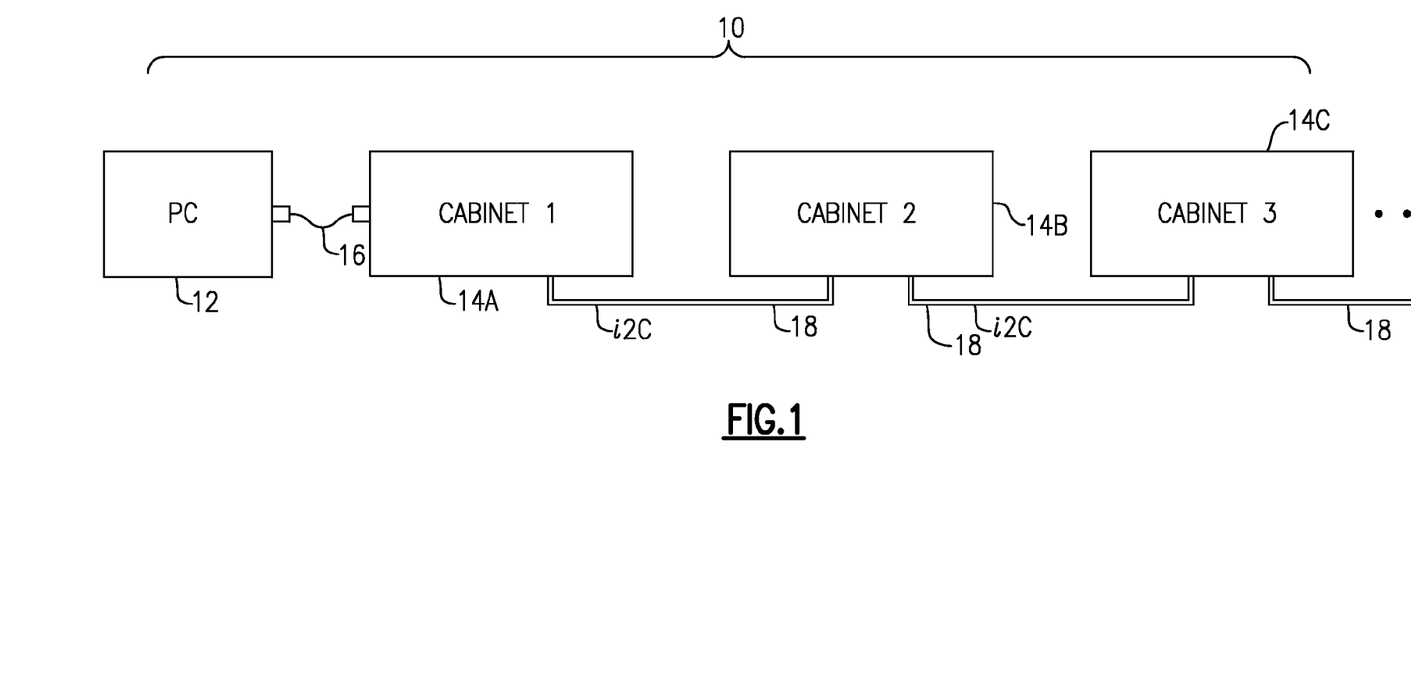
FIG. 1 is a general schematic view of a daisy-chained array of medical storage and medical supply cabinets according to the present invention.

With reference initially to FIG. 1 of the Drawing, an arrangement 10 of individual locking cabinets uses a daisy-chain wiring connection with i2C protocol communications to interconnect the cabinets with an associated computer 12, that serves as an interface to the array of cabinets 14A, 14B, 14C etc, with the computer connected, e.g., using a USB cable 16, to a first cabinet 14A of the array, and with the daisy-chain i2C wiring 18 connecting the first cabinet 14A to all the remaining cabinets 14B, 14C, etc. The term "i2C" refers to inter-integrated circuit protocol, involving a multi-master, single-ended computer bus that can be used to connect low-speed, intermediate speed, and high speed peripheral devices to a digital controller, e.g., computer. The number of peripherals in a single daisy chain is determined by the size of the message address space. If the address space is seven bits, this can permit up to sixty-four devices to be controlled and queried by a single control computer.

Each cabinet 14A, 14B, 14C may have one or more individually locking storage compartments, e.g., locking doors and/or drawers. Each cabinet may be individually powered, i.e., from wall outlet power or from battery power, or may be powered with electrical power supplied by the daisy chain cable 18. The daisy-chain cables 18 have three (or more) conductors, including a common conductor plus conductors supplying serial data and serial clock. Additional conductors may supply power or ground. The messages sent between the computer 12 and the individual cabinets represented here are used to control the individual locking and unlocking of the doors and/or drawers of the cabinet, and are also used to send status messages back to the computer 12.

This arrangement 10 of cabinets enables a facility, such as a medical clinic, hospital or pharmacy, to connect multiple cabinets into a single drug-dispensing and medical item supply system to be run from a computer 12 at a single location, and allows the arrangement to be enlarged by adding one or more cabinets into the system, with the added cabinets being recognized automatically by the computer 12 and immediately integrated into the array, without user input to the computer.

The cabinets 14A, 14B, 14C may all be identical in that any one of them may be the cabinet that is connected with the computer 12, here using a cable 16 plugged into the computer's USB port. The daisy-chain cabling 18 then connects the cabinet 14A that is directly to the computer 12 to a nearby cabinet 14B, which is connected in turn to a third cabinet 14C. Many further cabinets can be added to the daisy chain, and may be located throughout the facility. While a USB cable 16 is shown here for interconnecting the computer 12 with the cabinet 14A, other wired communications cabling could be used, as could a wireless connection, e.g., infrared or Bluetooth. Each cabinet 14A, 14B, 14C has a facility for securing medications or supplies, either with doors, drawers, or bins. These doors, drawers, or bins can be secured with solenoid locks or with rotary latches or motor-and-hook assemblies. One or more of the cabinets may also include a locking refrigerator for storing temperature-sensitive materials. The locking refrigerator may be controlled using a USB cable connected, e.g., to the control circuit board of the associated cabinet, or may be controlled as a part of the daisy-chain i2C communications. The cabinets may also be provided with LED lighting or other lighting that is controlled by the cabinet 14A, 14B, 14C or by the computer 12 through the daisy-chain system. The drawers, doors, and/or bins have sensors to detect if they are open or closed, so the status can be reported back to the computer. An alarm, e.g., a buzzer, can be actuated in the event that a cabinet is left open for longer than some predetermined period. Also, the locks can have a manual override, e.g., a key-cylinder arrangement, to permit emergency access by authorized persons in the event of a power failure, or of a failure of the computer or the daisy-chain system.

Figure 2:
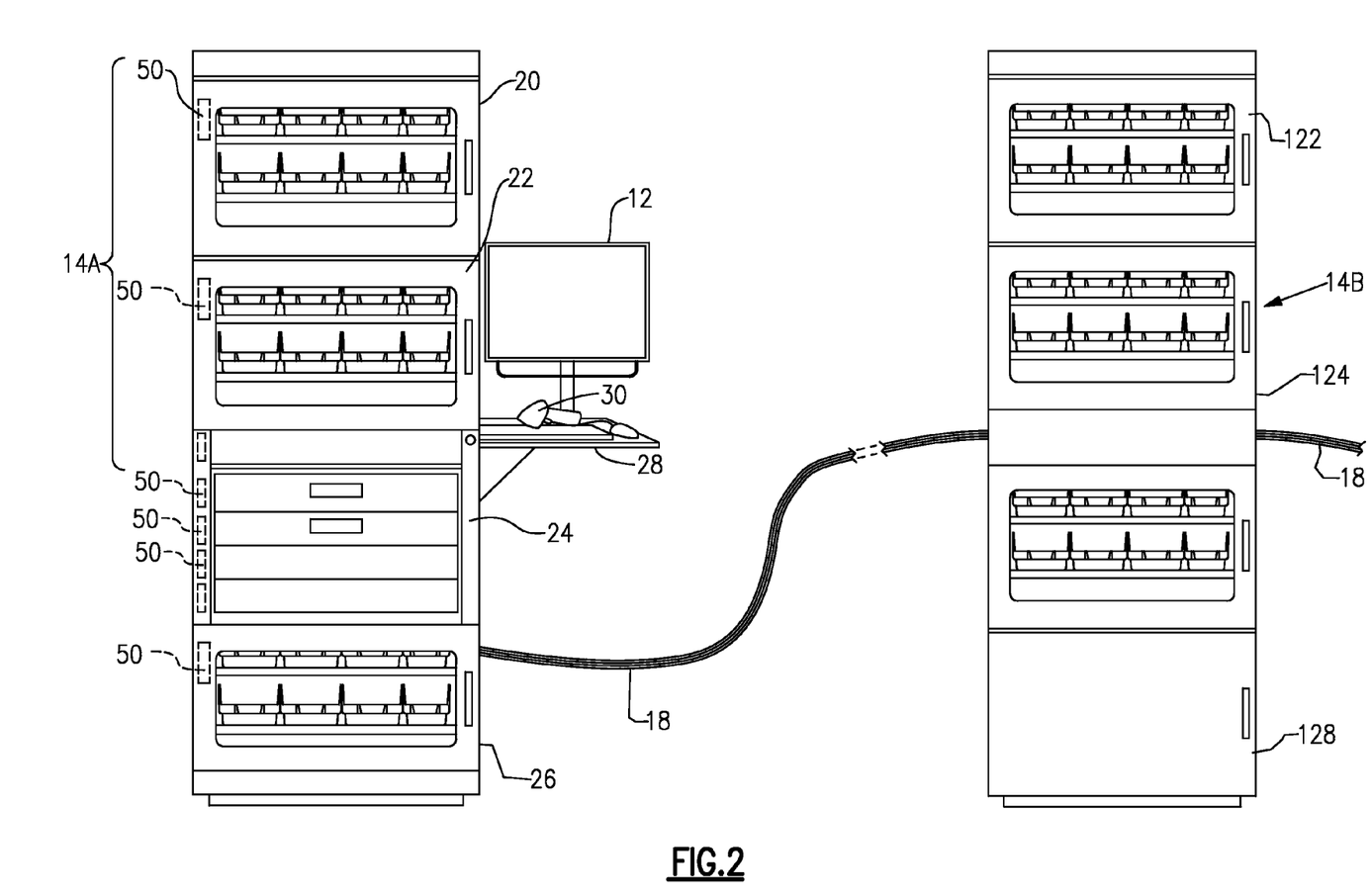
FIG. 2 is a perspective view of a medical cabinet a part of an array according to one preferred embodiment of this invention.

FIG. 2 shows the first two of these medical supply or medication storage cabinets 14A and 14B in the daisy-chain array. The first cabinet 14A has a group of locking compartments positioned vertically one above the other, here with a first compartment 20 at the top and a second compartment 22 just beneath, each with a locking door that has a transparent window through which the contents can be viewed. Beneath these is a set of four locking pull-out drawers 24, and then at the base thereof another locking compartment 26 with locking door. At the right side of the cabinet 14A is a computer shelf 28, on which the computer 12 is placed. The computer may use keyboard and mouse to enter data, or may use an active touch screen to interface with the nurse or pharmacist. In this embodiment, there is an associated bar-code scanner 30, which can be used for verifying the identity of a person who accesses the system by scanning the person's badge or identity card. The computer 12 is directly connected to this cabinet 14A, and this first cabinet is connected to the second cabinet 14B by means of an i2C daisy-chain cable 18. The second cabinet is shown here having three locking-door compartments 122, 124 and 126, plus a refrigerated compartment 128 where temperature sensitive materials, such as certain vaccines for example, may be stored. Then another daisy-chain cable 18 continues from this cabinet 14B to another cabinet, not shown in this view. A stand-alone medical refrigerator could easily be integrated into the daisy-chain array 10.

Figure 3:
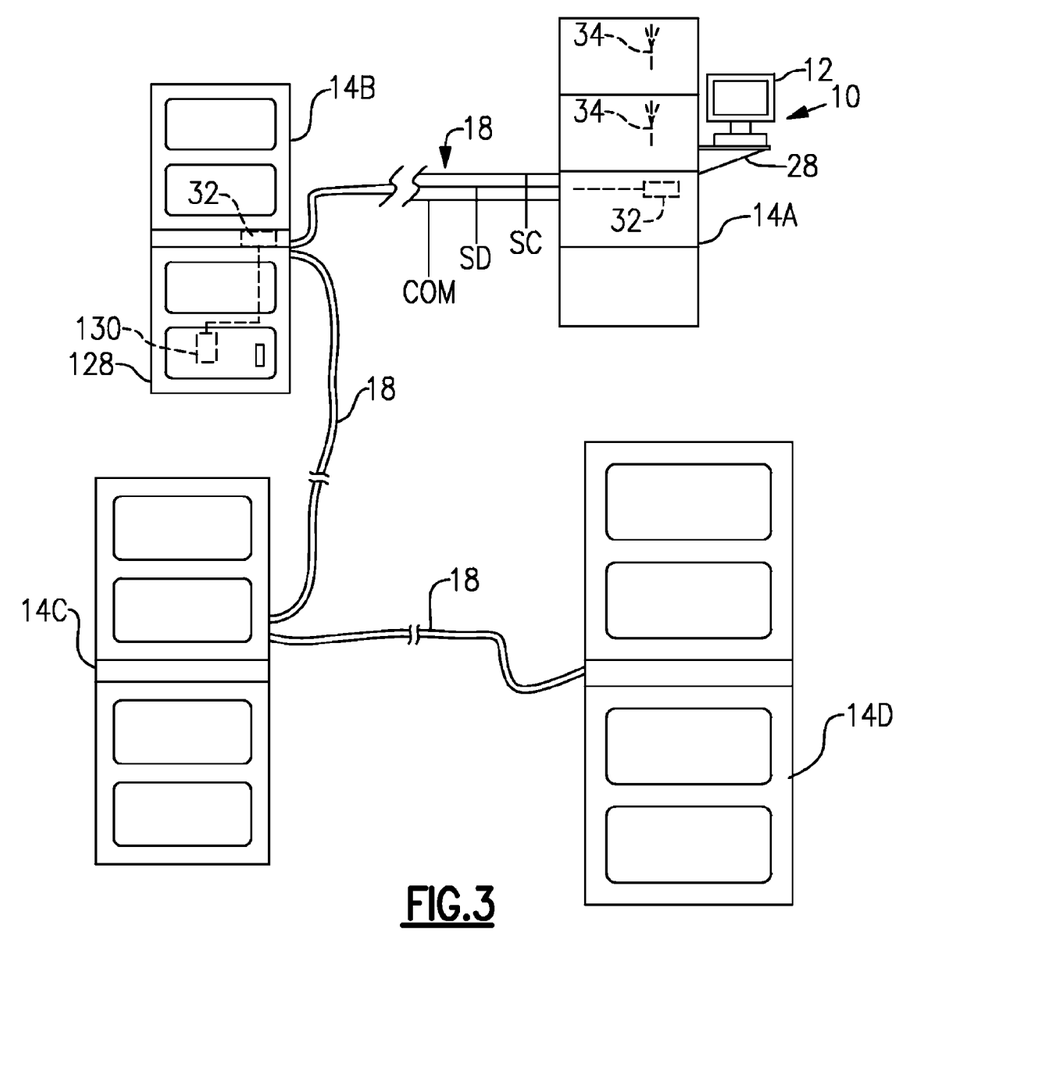
FIG. 3 is another perspective view of the medical cabinet array.

As shown more schematically in FIG. 3, the first cabinet 14A includes a controller module 32, which has a computer port, e.g., a USB port, that connects to the computer 12, and has other connections to going to servo motors for locking and unlocking the respective compartments and drawers, and also going to sensors to detect whether the doors and/or drawers are in an open state or a closed state. As shown somewhat symbolically here, the cabinet includes one or more RFID antennas 34 that are also coupled to the controller module 32 and make it possible to scan any RFID-tagged items, such as pharmaceutical containers, or catheters, or dressings, which may be contained within the cabinet or within a specific compartment or drawer. Finally, the module 32 includes an i2C port to which the daisy-chain communications cable 18 is connected to interconnect this module 32 with similar modules in each of the remaining cabinets 14B, 14C, through 14D. The cable 18 has three (or more) conductors, including at least a common conductor COM, a serial data conductor SD, and a serial clock conductor SC.

In the second cabinet, the refrigerated compartment 128 includes a temperature sensor 30 that provides temperature data to the controller module 32 of the second cabinet 14B. There may be other sensors present as well, for example, a humidity sensor.

Figure 4:
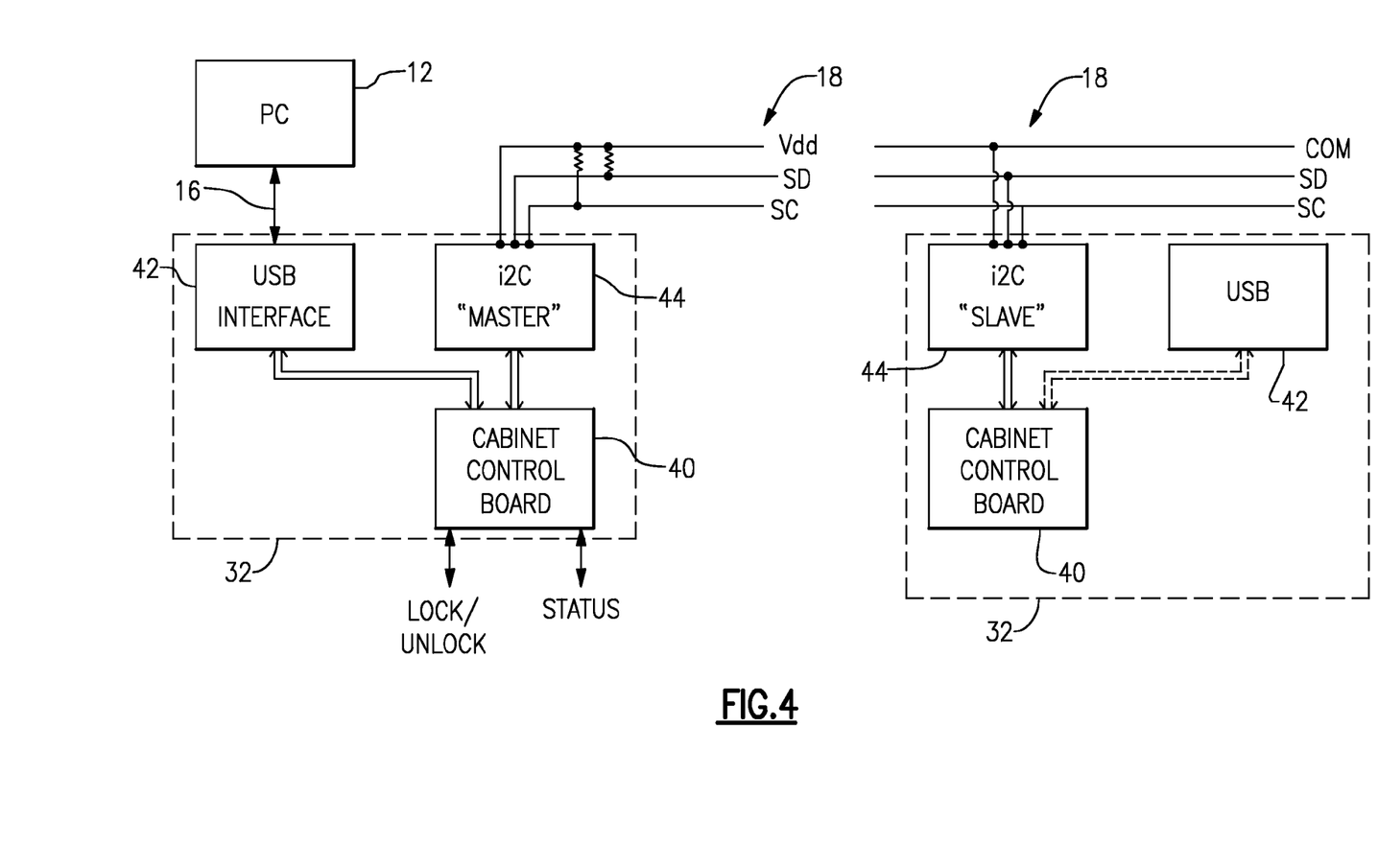
FIG. 4 is a schematic diagram of the control circuit modules as employed in this embodiment.

As shown in the schematic view of FIG. 4, the control module 32 for the first cabinet 14A has a cabinet control board including modules for locking and unlocking the various doors, drawers, or bins, e.g., by actuating servo motors or solenoids, and for obtaining status of the various compartments, including open/closed status, lights on/off, RFID inventory, or temperature (in the case of the refrigerated compartment 128). The control board 40 is connected to a USB interface communications port 42, which allows connection to the computer 12, and is also connected to an i2C communications port 44, which allows connection to the daisy chain cable 18. In each other cabinet that is installed in the daisy chain array there is a similar control module 32, as shown at the right-hand side of FIG. 4, which has an identical cabinet control board 40 and i2C port 44 to connect with the conductors of the daisy chain cable 18. Each control module also includes a USB interface port 42 as well, so that any of the cabinets can be connected with a computer that is properly configured and programmed to control the locking and unlocking of all of the cabinets, and can obtain status from all of the cabinets. In FIG. 4, the i2C port 44 in the control module 32 that is directly connected to the computer 12 is labeled as "master" and the other i2C port 44 is labeled as "slave". However, each of these is capable of serving in either a master role or slave role.

Additional cabinets of the same type can be installed in the daisy chain arrangement 10, with access controlled by the same computer 12, by simply attaching a daisy chain cable from that cabinet to any other cabinet. When this is done, the computer will immediately recognize that an additional cabinet has been installed and will assign the cabinet a unique serial number and address code, and obtain data resident on that cabinet. This permits the computer to lock and unlock the compartments on the added cabinet, and to query status, e.g., inventory and open/closed status of doors or drawers.

The computer 12 can be used to turn illumination on and off for the specific compartments in the cabinets, e.g., LED lighting modules 50 (FIG. 2). The lighting modules may be in one or the front columns of the cabinet, shining back into the compartment, allowing a given compartment to be individually illuminated.

Figure 5:
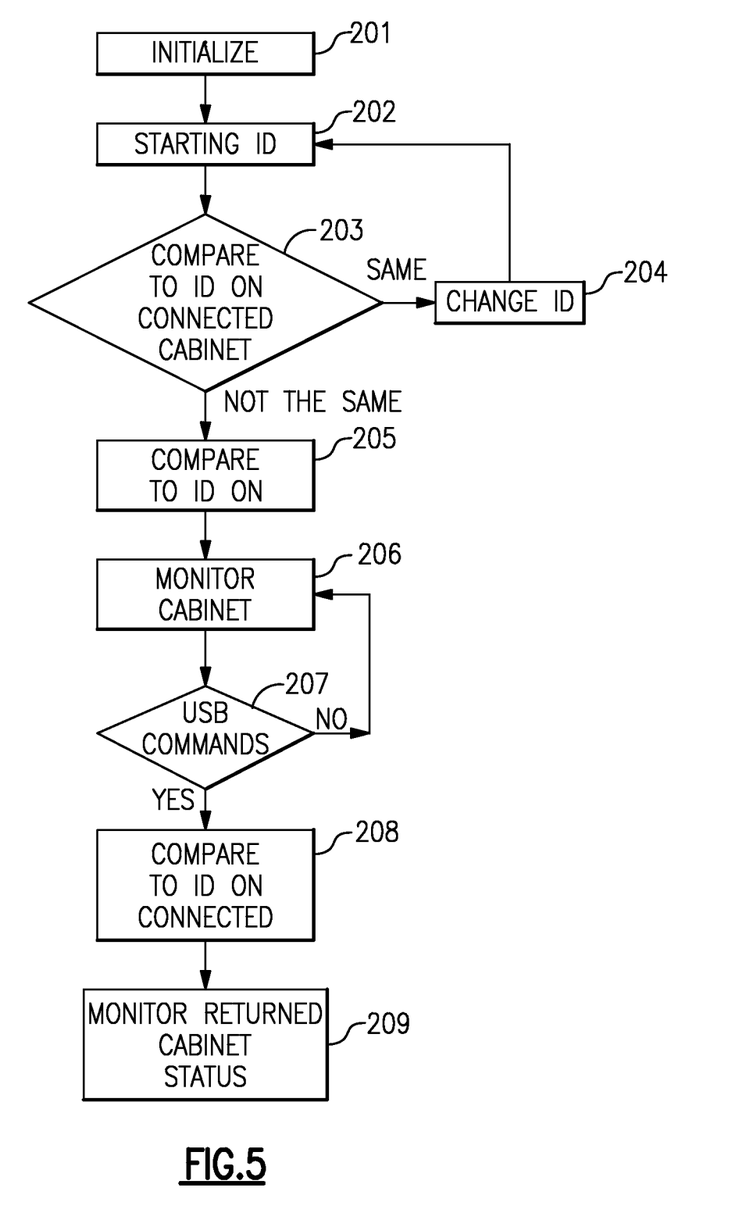
FIG. 5 is a logic diagram for explaining the operating procedures of this embodiment.

As shown in the logic chart of FIG. 5, as soon as a new cabinet is connected onto the daisy chain cable 18, the computer recognizes this, and initializes a set up procedure [step 201]. The computer assigns a starting ID code or serial number for the new cabinet [step 202] and compares this to the ID codes on the connected cabinets [step 203]. If the initial code matches any of these then a new or changed ID code is assigned [step 204] and the previous step 203 is repeated. If the ID code is not the same as any already assigned, i.e., if it is unique, then the ID code is assigned to the new cabinet [step 205]. The new cabinet is now ready for the computer 12 to monitor it, together with the other cabinets in the daisy chain array [step 206]. The control circuit module in the first cabinet is continuously awaiting commands sent from the computer [step 207] but continues to monitor all the cabinets [step 206] until the computer issues a command, which can be issued to a specific address or to the general call address. When a command is issued, the daisy chain i2C protocol communicates the command to the addressed cabinet [step 208], after which the computer monitors for a return report of cabinet status from the addressed cabinet (or cabinets) [step 209]. The added cabinet needs no set-up to start receiving commands for locking or locking or to provide cabinet status. Alternatively, the cabinets can be set up remotely (that is, from the computer 12) to have full status functions, such as name, location, and inventory control. This arrangement provides a durable, reliable lock and unlock mechanism for remotely controlling access to the medications and medical supplies and can be achieved at low to moderate cost.

Any additional cabinets can be added at any point by breaking the daisy chain, and connecting the new cabinet to the disconnected cable and adding an additional cable to the next cabinet. Either a ring wiring or linear topology may be used.

The cabinets can be configured to provide status automatically as soon as there is a change in status, or at periodic intervals, or when queried or polled by the computer 12.

While the invention has been described hereinabove with reference to a preferred embodiment, it should be recognized that the invention is not limited to that precise embodiment. Rather, many modification and variations would present themselves to persons skilled in the art without departing from the scope and spirit of this invention, as defined in the appended claims.

What is claimed is:

1. A daisy-chain array of controlled access medication storage cabinets comprising
a plurality of medication cabinets, each said medication cabinet including at least one electronically controlled locking compartment, which may be closed to secure contents within the locking compartment and opened for access to said contents, and which may be locked and unlocked;
a control circuit module coupled to said at least one locking compartment to transmit lock and unlock commands thereto and to obtain therefrom open/closed status of the locking compartment and locked/unlocked status of the locking compartment; and having a computer connection port for connecting to a suitably programmed computer, and an i2C port adapted to be connected to the other cabinets in the array and adapted to receive at least suitably addressed lock commands and unlock commands and to transmit status messages;
a daisy-chain cable connected with the i2C ports of each of the cabinets of said array, the cable including at least a common conductor, a serial clock conductor, and a serial data conductor;
a suitably programmed computer connected by a wire or wireless connection to the computer connection port of the control circuit module of one of said medication cabinets, and serving as a control interface for each of the cabinets in said array, and being suitably programmed to assign a unique identification code to each said cabinet in said array, to transmit command codes that incorporate said identity codes to specific ones of the cabinets, including a command to lock the at least one locking compartment thereof, a command to unlock the at least one locking compartment thereof, and a status request, and to receive responses from said cabinets to include an open or closed status of the at least one locking compartment and a locked or unlocked status of the at least one locking compartment;
and wherein one or more additional cabinets can be added later to said array by connecting the i2C port thereof to the i2C port of any of the plurality of medication cabinets in said array, and wherein said suitably programmed computer is configured for automatically recognizing the presence of the additional cabinet and for automatically assigning each such additional cabinet a unique identity code as an added member of said array.

2. The array of controlled access medication storage cabinets according to claim 1 wherein said at least one locking compartment includes a plurality of compartments having locking doors.

3. The array of controlled access medication storage cabinets according to claim 2 wherein said suitably programmed computer transmits commands containing the unique identifying code of a target cabinet of said plurality of medication storage cabinets, and a unique code identifying a specific one of said plurality of locking doors for the cabinet to unlock.

4. The array of controlled access medication storage cabinets according to claim 1 wherein said at least one locking compartment includes a plurality of locking drawers.

5. The array of controlled access medication storage cabinets according to claim 4 wherein said suitably programmed computer transmits commands containing the unique identifying code of a target cabinet of said plurality of medication storage cabinets, and a code identifying a specific one of said plurality of locking drawers for the cabinet to unlock.

6. The array of controlled access medication storage cabinets according to claim 1 wherein said at least one locking compartment includes an RFID reader adapted to read RFID tags on medical items within the compartment and means coupling the RFID reader to the associated control circuit module so that the latter may conduct an inventory of medical items within said cabinet, and transmit inventory data automatically upon a change in said inventory from the i2C port thereof to said suitably programmed computer.

7. The array of controlled access medication storage cabinets according to claim 1 wherein said suitably programmed computer sends data messages to at least one of the cabinets in said array containing identification of the cabinet and location of the cabinet.

8. The array of controlled access medication storage cabinets according to claim 1 wherein at least one of said cabinets includes a respective illumination system to provide lighting within each of the locking compartments thereof, and wherein said suitably programmed computer transmits commands with identification code of said at least one cabinet and codes identifying which of the associated illumination systems are to be energized.

9. The array of controlled access medication storage cabinets according to claim 1 wherein at least one of the cabinets of said array includes a refrigerated storage compartment with a locking compartment door, and with a temperature sensor within said refrigerated storage compartment electrically coupled to the control circuit module of the associated medication storage cabinet, and such control circuit module being adapted to provide a status message including temperature data to said suitably programmed computer.

10. The array of controlled access medication storage cabinets according to claim 1 wherein said suitably programmed computer provides command messages containing a general call identification code, and wherein the control circuit modules for all of the medication storage cabinets of said array are adapted to respond to the command messages containing said general call identification code.

11. The array of controlled access medication storage cabinets according to claim 1 in which each of said control circuit modules includes programming that is installed and resident thereon, and the control circuit modules are each adapted to provide a status response to said suitably programmed computer including revision information concerning the programming resident on the control circuit module.

12. The array of controlled access medication storage cabinets according to claim 1 wherein the associated control circuit module of each of the plurality of cabinets in the array is capable of being connected with said suitably programmed computer and is capable of serving in either a master mode or slave mode, such that the array is configured to permit any of the storage cabinets in the array to serve as host to said suitably programmed computer.

13. The array of controlled access medication storage cabinets according to claim 1 wherein said suitably programmed computer assigns a general code to each cabinet in the array to permit the suitably programmed computer to issue a general call to all the cabinets in the array, and wherein the suitably programmed computer automatically assigns said general code to each additional cabinet added to the array.

* * * * *